United States Patent [19]

Schönafinger et al.

[11] Patent Number: 5,015,659
[45] Date of Patent: May 14, 1991

[54] THIENYLACETIC ACID DERIVATIVES, PROCESS FOR THE PREPARATION THEREOF, THE USE THEREOF, AND PHARMACEUTICALS CONTAINING THESE AND THE PREPARATION THEREOF

[75] Inventors: Karl Schönafinger, Alzenau; Rudi Beyerle, Frankfurt; Ursula Schindler, Mörfelden-Walldorf; Bernd Jablonka, Oberursel, all of Fed. Rep. of Germany; Jeffery Troke, Newport Pagnell, England

[73] Assignee: Cassella Aktiengesellschaft, Frankfurt, Fed. Rep. of Germany

[21] Appl. No.: 495,439

[22] Filed: Mar. 14, 1990

[30] Foreign Application Priority Data

Mar. 16, 1989 [DE] Fed. Rep. of Germany ....... 3908547

[51] Int. Cl.$^5$ ..................... A61K 31/38; C07D 333/22
[52] U.S. Cl. ........................................ 514/438; 549/76
[58] Field of Search ........................... 549/76; 514/438

[56] References Cited

FOREIGN PATENT DOCUMENTS 0067641 12/1982 European Pat. Off. ............. 549/76

*Primary Examiner*—Alan Siegel
*Attorney, Agent, or Firm*—Perman & Green

[57] ABSTRACT

The present invention relates to thienylacetic acid derivatives of the general formula I

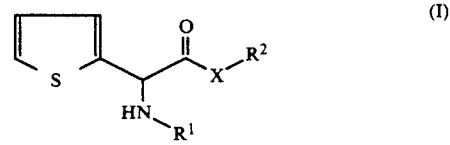

in which
X denotes —O— or —NH—;
$R^1$ denotes hydrogen, the group —CH$_2$—CO—R$^3$ or the group —CO—CH$_2$—NH$_2$;
$R^2$ denotes hydrogen, (C$_1$–C$_4$)-alkyl or the radical $R^1$ and
$R^3$ denotes (C$_1$–C$_4$)-alkoxy, hydroxyl or amino, it not being possible for both $R^1$ and $R^2$ to represent hydrogen when X denotes O, as well as the pharmaceutically tolerated salts thereof, process for the preparation thereof, the use thereof, and pharmaceuticals containing these and the preparation thereof.

6 Claims, No Drawings

THIENYLACETIC ACID DERIVATIVES, PROCESS FOR THE PREPARATION THEREOF, THE USE THEREOF, AND PHARMACEUTICALS CONTAINING THESE AND THE PREPARATION THEREOF

BACKGROUND OF THE INVENTION

1. Field of the Invention

The present invention relates to novel pharmaceutical compounds derived from thienylacetic acid, and to processes for the preparation of such compounds. The invention also relates to pharmaceutical compositions containing the present compounds, and to the preparation and use of such compositions for the treatment of disorders of brain functions or for controlling cerebral aging processes.

2. Description of the Art

The novel compounds and compositions of the present invention have been found to be considerably superior to hitherto known compounds used for similar purposes, such as piracetam, aniracetam and oxiracetam, which are not thienylacetic acid derivatives.

The closest known chemically-related thienylacetic acid compounds are the starting compounds 2-thienylglyoxylic acid and 2-thienylglycin (formula V) which are commercially available. They are not known to display encephalotropic or nootropic effects or to be useful for treatment of brain disorders.

SUMMARY OF THE INVENTION

The present invention relates to thienylacetic acid derivatives of the general formula I

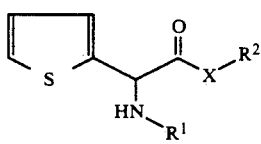

in which

X denotes —O— or —NH—;

$R^1$ denotes hydrogen, the group —CH$_2$—CO—R$^3$ or the group —CO—CH$_2$—NH$_2$;

$R^2$ denotes hydrogen, (C$_1$-C$_4$)-alkyl or the radical $R^1$ and $R^3$ denotes (C$_1$-C$_4$)-alkoxy, hydroxyl or amino, it not being possible for both $R^1$ and $R^2$ to represent hydrogen when X denotes O, as well as the pharmaceutically tolerated salts thereof.

(C$_1$-C$_4$)-alkyl representing $R^2$, and the alkyl radical of (C$_1$-C$_4$)-alkoxy representing $R^3$, are straight-chain or branched and denote methyl, ethyl, n-propyl, i-propyl, n-butyl, i-butyl or tert.-butyl. Methyl, ethyl and tert.-butyl are preferred.

Pharmaceutically tolerated salts are preferably acid addition salts, particularly preferably the hydrochlorides.

Preferred compounds of the general formula I are those in which

X denotes —O—;

$R^1$ denotes the group —CH$_2$—CO—R$^3$;

$R^2$ denotes hydrogen or (C$_1$-C$_4$)-alkyl and $R^3$ denotes (C$_1$-C$_4$)-alkoxy, hydroxyl or amino.

Likewise preferred are those compounds of the general formula I in which

X denotes —NH—;

$R^1$ denotes the group —CH$_2$—CO—R$^3$;

$R^2$ denotes hydrogen and $R^3$ denotes (C$_1$-C$_4$)-alkoxy or hydroxyl.

2-Thienyl-N-aminocarbonylmethylaminoacetic acid and 2-thienyl-N-hydroxycarbonylmethylaminoacetamide hydrochloride are particularly preferred.

Compounds of the general formula I can be prepared, for example, by converting a compound of the general formula II

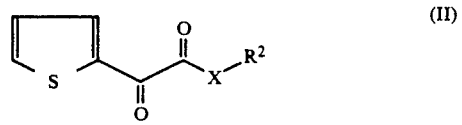

in which X and $R^2$ are as defined above, with hydroxylamine into the oxime and the latter by reduction into the compound of the general formula Ia according to the invention

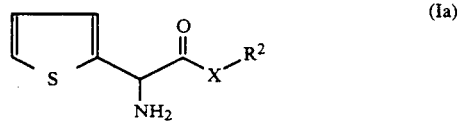

it being possible to convert the latter where appropriate (a) by alkylation with halogenoacetic esters of the general formula III

in which

Hal denotes halogen, preferably bromine, and $R^4$ denotes (C$_1$-C$_4$)-alkyl, into other compounds of the general formula Ib according to the invention

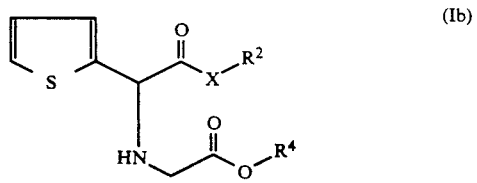

and the latter by hydrolysis or ammonolysis with ammonia into other compounds of the general formula Ic according to the invention

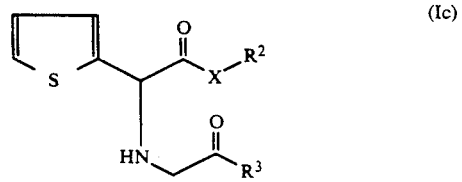

in which $R^3$ denotes —OH or —NH$_2$, or (b) by reaction with the mixed anhydride of the formula IV

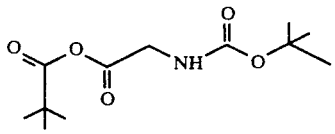

and subsequent hydrolysis into the compounds of the formula Id according to the invention

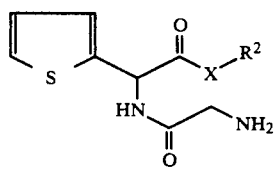

it being possible for the compounds of the general formulae Ia to Id according to the invention also to be converted into a salt where appropriate.

The compounds of the general formula II can be obtained, for example, from 2-thienylglyoxylic acid, which can be bought, by esterification or amidation or from the esters thereof, such as, for example, from ethyl 2-thienylglyoxylate by transesterification or aminolysis with appropriately substituted alcohols or primary amines. The compound of the general formula III, and the said alcohols and primary amines, are known and can be prepared by customary methods.

The compound of the formula IV is known and is advantageously prepared in situ from N-tert.-butoxycarbonylglycine and trimethylacetyl chloride.

Another method for the preparation of compounds of the general formula I according to the invention comprises esterifying or amidating 2-thienylglycine of the formula V

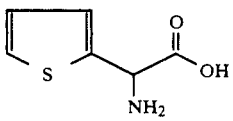

to give compounds of the general formula Ia according to the invention, and where appropriate further reacting the latter as described above in (a) and (b).

The compound 2-thienylglycine can be bought.

It is also possible, where appropriate, for the sequence of process steps in the specified synthetic possibilities to be altered.

All the process steps described for the preparation of the compounds of the general formula I, such as, for example, esterifications, transesterifications, ammonolyses, aminolyses, amidations, alkylations, hydrolyses and reductions, are known per se to those skilled in the art and described in all current textbooks of organic chemistry, for example in Houben-Weyl, "Methoden der Organischen Chemie" (Methods of Organic Chemistry).

The reduction of the compound obtained by reaction of the compound of the formula II with hydroxylamine is preferably carried out in alcohols as solvents. Methanol and ethanol are particularly preferred. The reaction temperatures are preferably 30°–120° C. Palladium and platinum catalysts are preferably used as catalyst, particularly preferably Raney nickel.

Alkylations of compounds of the general formula Ia with halogenoacetic esters of the general formula III are preferably carried out at temperatures of 0°–100° C. All inert solvents are preferred as solvents, particularly preferably ether, DMF and DME. The subsequent hydrolysis to give compounds of the general formula Ic is preferably carried out in inert solvents, particularly preferably in alcohols and ethers, at temperatures of, preferably, 0° C. to the boiling point of the solvent used.

Alkylations of compounds of the general formula Ia with the mixed anhydride of the formula IV are preferably carried out in inert solvents, particularly preferably in DMF or ether, at temperatures of, preferably, −20° to +60° C., particularly preferably at −20° C. to room temperature. The hydrolysis which follows this is preferably carried out with acid, for example with hydrogen chloride or trifluoroacetic acid, preferably at temperatures of 0° to 50° C., particularly preferably at room temperature.

Where the compounds of the general formula I according to the invention contain basic residues, they form acid addition salts with inorganic or organic acids. Suitable for forming acid addition salts of this type are inorganic and organic acids. Examples of suitable acids are: hydrogen chloride, hydrogen bromide, naphthalenedisulphonic acids, especially naphthalene-1,5-disulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, nicotinic, isonicotinic, methanesulphonic, p-toluenesulphonic, citric or adipic acid. Pharmacologically acceptable acid addition salts are preferred. The acid addition salts are prepared as customary by combining the components, expediently in a suitable solvent or diluent. It is possible in the synthesis of the compounds of the general formula I for the acid addition salts to be produced first in the course of working up. The free compounds of the general formula I can be obtained if desired from the acid addition salts in a known manner, for example by dissolving or suspending in water and making alkaline, for example with sodium hydroxide solution, and subsequently isolating.

Compounds of the general formula I which have a carboxyl group can also be in salt form. The sodium, potassium and ammonium salts are preferred and can be obtained by reacting the acid form with appropriate bases. If the compounds of the general formula I also contain a free amino group in addition to a carboxyl group, they can also be in the form of inner salts.

The compounds of the general formula I according to the invention, and the pharmaceutically tolerated salts thereof, have valuable pharmacological properties. They have CNS activity, for example they display encephalotropic and nootropic effects and are used for the treatment of disorders of brain functions such as cerebral insufficiency, cerebral ageing processes, diminished memory efficiency as also occur in Alzheimer's disease or multiinfarct dementia or in diminished learning efficiency. Surprisingly, they are considerably superior to the hitherto known compounds acting in the same direction. They display an excellent activity in a variety of tests such as, for example, in the prolongation of survival time under sodium nitrite hypoxia (Gibsen and Bless, J. Neurochemistry 27, (1976)), in the improvement in nitrogen-induced hypoxia tolerance, where experimental animals are, after premedication with the investigated products, ventilated with pure nitrogen, and the prolongation of the period between starting ventilation and electrical neutrality of the electroencephalogram, and the lethality, are measured.

The products according to the invention also have very good activity in tests which are directly aimed at measuring learning and memory efficiency such as, for example, the known avoidance tests.

Testing in the tests mentioned, and in a number of others, reveals that the compounds according to the invention surprisingly have, in low doses, together with a low toxicity, a particularly beneficial profile of effects not present in this form in known products. The following tables are intended to show this in detail:

1) Scopolamine-induced amnesia in the mouse

Injection of a scopolamine dose of 3 mg/kg i.p. leads to an amnesia in a passive-avoidance learning test. Oral pretreatment with the compounds of the general formula I can, as the following table shows, significantly antagonize the experimentally induced amnesia. The known substance piracetam has, by comparison with this, only marginal activity.

| Example No. | Dose mg/kg oral | Scopolamine amnesia % reversal of amnesia |
|---|---|---|
| 5 | 30 | 56 |
| 8 | 30 | 71 |
| Piracetam (comparison) | 30 | 18 |

2) Ischaemia-induced amnesia in the Mongolian gerbil

Brief bilateral cerebral ischaemia (3-5 min) in the gerbil leads to a prolonged learning impairment in passive-avoidance learning. The learning impairment can be antagonized if the animals are treated intraperitoneally with the compounds of the general formula I immediately after the end of ischaemia. The table which follows indicates the dosages which elicit a half-maximum (about 50%) antagonism of the learning impairment. The compounds according to the invention show a pronounced superiority to the compounds of the state of the art.

| Example No. | Dose mg/kg ip | Ischaemia-induced learning impairment % reversal of learning impairment |
|---|---|---|
| 5 | 1.00 | 51 |
| 8 | 0.03 | 58 |
| 9 | 0.10 | 54 |
| 11 | 1.00 | 54 |
| Aniracetam (comparison) | 30.00 | 45 |
| Oxiracetam (comparison) | 100.00 | 46 |

3) Receptor-binding studies in vitro

Examination of the action of the substances of the general formula I according to the invention on the binding constants of the glycine receptor in rat cortex synaptosomes reveals a pronounced specific binding. The known substance piracetam is inactive.

| Example No. | Binding to glycine receptors in the brain |
|---|---|
| 9 | $K_d = 1.8 \times 10^{-6}$ M |
| 11 | $K_d = 1.8 \times 10^{-6}$ M |
| Piracetam | No specific binding |

-continued

| Example No. | Binding to glycine receptors in the brain |
|---|---|
| (comparison) | |

The compounds of the general formula I and the physiologically tolerated salts thereof thus represent an enrichment of pharmacy.

The compounds of the general formula I according to the invention and the pharmaceutically tolerated salts thereof can thus be used in humans as medicines, for example for controlling or preventing disorders based on an impairment of brain function and for the treatment and prevention of cerebral ageing processes.

The compounds of the general formula I and the pharmaceutically tolerated salts thereof can be administered as medicines alone, mixed with one another or in the form of pharmaceutical preparations which allow enteral or parenteral administration and which contain as active ingredient an effective dose of at least one compound of the general formula I or of a salt thereof, in addition to customary pharmaceutically acceptable vehicles and additives. The preparations normally contain about 0.5 to 90% by weight of the therapeutically active compound.

The medicines can be administered orally, for example in the form of pills, tablets, lacquered tablets, coated tablets, granules, hard and soft gelatin capsules, solutions, syrups, emulsions or suspensions or aerosol mixtures. The administration can, however, also take place rectally, for example in the form of suppositories, or parenterally, for example in the form of injection solutions, or percutaneously, for example in the form of ointments or tinctures.

The pharmaceutical products are prepared in a manner known per se, using pharmaceutically inert inorganic or organic vehicles. It is possible to use for the preparation of pills, tablets, coated tablets and hard gelatin capsules, for example lactose, maize starch or derivatives thereof, talc, stearic acid or salts thereof etc. Examples of vehicles for soft gelatin capsules and suppositories are fats, waxes, semisolid and liquid polyols, natural or hardened oils etc. Examples of suitable vehicles for the preparation of solutions and syrups are water, sucrose, invert sugar, glucose, polyols etc. Examples of suitable vehicles for the preparation of injection solutions are water, alcohols, glycerol, polyols, vegetable oils etc.

The pharmaceutical products can, besides the active compounds and vehicles, also contain additives such as, for example, fillers, extenders, disintegrants, binders, lubricants, wetting agents, stabilizers, emulsifiers, preservatives, sweeteners, colorants, flavourings or aromatizing agents, thickeners, diluents, buffer substances, as well as solvents or solubilizers or agents to achieve a depot effect, as well as salts to alter the osmotic pressure, coating agents or antioxidants. They can also contain two or more compounds of the general formula I or the pharmacologically acceptable acid addition salts thereof and, in addition, one or more other therapeutically active substances.

Examples of other therapeutically active substances of this type are agents to promote blood flow, such as dihydroergocristine, nicergoline, buphenine, nicotinic acid and esters thereof, pyridylcarbinol, bencyclane, cinnarizine, naftidrofuryl, raubasine and vincamine; positive inotropic compounds such as digoxin, acetydigoxin, metildigoxin and lanato glycosides; coronary dilators such as carbocromen, dipyridamole, nifedipine and perhexiline, antianginal compounds such as isosorbide dinitrate, isosorbide mononitrate, glycerol nitrate, molsidomine and verapamil, β-blockers such as propranolol, oxprenolol, atenolol, metoprolol and penbutolol. In addition, the compounds can be combined with other substances with nootropic activity, such as, for example, piracetam, or substances with CNS activity, such as pirlindole, sulpiride etc.

The dosage can be varied within wide limits and should be adjusted in each individual case to the individual circumstances. In general, a daily dose of about 0.1 to 1 mg/kg, preferably 0.3 to 0.5 mg/kg, of body weight is appropriate on oral administration to achieve effective results, and the daily dose on intravenous administration is generally about 0.01 to 0.3 mg/kg, preferably 0.05 to 0.1 mg/kg, of body weight. The daily dose is normally divided into several, for example 2, 3 or 4, partial administrations, especially when relatively large amounts are administered. It may be necessary where appropriate, depending on individual behaviour, to deviate from the stated daily dose in an upward or downward direction. Pharmaceutical products normally contain 0.1 to 50 mg, preferably 0.5 to 10 mg, of active compound of the general formula I or of a pharmacologically acceptable salt thereof per dose.

Examples 1 to 11 which follow relate to the preparation of compounds of the general formula I, and Examples A to H relate to the production of preparations of compounds of the general formula I.

EXAMPLE 1 tert.-Butyl 2-thienylaminoacetate

A mixture of 12.6 g of 2-thienylaminoacetic acid, 300 ml of dimethoxyethane, 15 ml of sulphuric acid and 100 ml of isobutene is stirred at room temperature in an autoclave for 5 h and poured into a mixture composed of 800 ml of ether and 800 ml of 1N sodium hydroxide solution. The ethereal phase is separated off, and the aqueous phase is extracted twice more by shaking with 200 ml of ether each time. After drying of the ether phases over $MgSO_4$ and evaporation of the solvent there remains a yellowish oily residue.

Yield: 6.8 g oil

EXAMPLE 2

Methyl 2-thienylaminoacetate HCl

Gaseous HCl is passed into a solution of 6.8 g of 2-thienylaminoacetic acid in 70 ml of methanol, and the mixture is heated at 50° C. for 6 h. The excess methanol and hydrochloric acid are stripped off in vacuo, and the solid residue is washed with methanol and dried in vacuo.

Yield: 5.9 g melting point 179° C.

EXAMPLE 3 tert.-Butyl 2-thienyl-N-methoxycarbonylmethylaminoacetate

A mixture of 6.6 g of tert.-butyl 2-thienylaminoacetate (Example 1), 3.3 g of triethylamine, 5.0 g of methyl bromoacetate and 40 ml of dimethoxyethane is refluxed for 4 h. The volatile fractions are removed in vacuo, the residue is stirred with 250 ml of water, and the product is extracted by shaking with ethyl acetate. After drying over $Na_2SO_4$, active charcoal is added, and the mixture is briefly boiled and filtered. Evaporation of the solvent leaves an oily residue.

Yield: 7.4 g oil

EXAMPLE 4 tert.-Butyl 2-thienyl-N-aminocarbonylmethylaminoacetate

A mixture of 7.4 g of the compound from Example 3 and 50 ml of concentrated methanolic ammonia is left to stand at room temperature for 15 h. The solvent is stripped off, the residue is treated with active charcoal in hot ethyl acetate, and the mixture is filtered. The residue remaining after evaporation of the solvent is stirred with diethyl ether, filtered off with suction and dried.

Yield: 3.2 g melting point 115°-117° C.

EXAMPLE 5

2-Thienyl-N-aminocarbonylmethylaminoacetic acid

Gaseous HCl is passed into a cooled solution of 2.4 g of the compound from Example 4 in 25 ml of glacial acetic acid until saturated. The mixture is allowed to reach room temperature while stirring. The precipitate which forms is filtered off with suction, washed with a little methanol and dried. Yield: 2.0 g melting point 206° C. (decomposition)

EXAMPLE 6

2-Thienylaminoacetamide a) 2-Thienylglyoxylamide 13.6 g of ammonia are passed into a cooled solution of 73.6 g of ethyl 2-thienylglyoxylate, and the resulting mixture is stirred at room temperature for 2 h. The solvent is stripped off in vacuo, and the residue is recrystallized from water:ethanol (80:20).

Yield: 40.3 g melting point 86°-88° C.

b) 2-Thienylhydroximinoacetamide

A mixture of 15.5 g of 2-thienylglyoxylamide, 75 ml of water, 75 ml of ethanol, 10.4 g of hydroxylamine hydrochloride and 24.6 g of sodium acetate is stirred at 40° C. for 5 h, the volatile fractions are stripped off in vacuo, and the residue is taken up in water. The product is extracted with ethyl acetate, and the organic phase is dried and concentrated. The residue is recrystallized from a little ethyl acetate.

Yield: 5.2 g melting point 146°-149° C.

c) 2-Thienylaminoacetamide

A mixture of 5.1 g of 2-thienylhydroximinoacetamide and 180 ml of methanol is hydrogenated in the presence of Raney nickel at 100° C./50 bar. After hydrogen uptake has ceased, the Raney nickel is filtered off with suction, the filtrate is concentrated, and the residue is recrystallized from diethyl ether.

Yield: 2.6 g melting point 82°-84° C.

EXAMPLE 7

2-Thienyl-N-tert.-butoxycarbonylmethylaminoacetamide

A solution of 9.4 g of 2-thienylaminoacetamide (Example 6), 12.9 g of tert.-butyl bromoacetate and 6.7 g of triethylamine in 100 ml of dimethoxyethane is boiled for 16 h. The residue remaining after concentration is partitioned between water and ethyl acetate. The ethyl acetate phase is dried, boiled with active charcoal, filtered and concentrated. The residue is recrystallized from ethyl acetate.

Yield: 3.4 g melting point 94°–95° C.

EXAMPLE 8

2-Thienyl-N-hydroxycarbonylmethylaminoacetamide hydrochloride

Gaseous HCl is passed into a stirred and cooled suspension of 3.2 g of the compound from Example 7 in 30 ml of glacial acetic acid until saturated. The mixture is then stirred for 1 h and the volatile fractions are removed in vacuo. The residue is recrystallized from ether.

Yield: 2.9 g melting point 208° C. (decomposition)

EXAMPLE 9

2-Thienyl-N-aminoacetylaminoacetic acid hydrochloride a) tert.-Butyl 2-thienyl-N-tert.-butoxycarbonylaminoacetylaminoacetate N-tert.-butoxycarbonylglycine (4.3 g) and 2.5 g of triethylamine are dissolved in 240 ml of tetrahydrofuran and cooled to −20° C. Then 2.9 g of trimethylacetyl chloride are added dropwise, and the mixture is stirred at −20° C. for 30 min. A solution of 7 g of the compound from Example 1 and 2.5 g of triethylamine in 20 ml of dimethylformamide is added dropwise to this mixture. The cold bath is removed, and the mixture is stirred at room temperature for 2 h. The precipitate is filtered off with suction, and the filtrate is concentrated. The oily residue is dissolved in ethyl acetate, and the solution is washed twice with 100 ml of water each time, once with 100 ml of 5% strength sodium bicarbonate solution and once with 100 ml of 1 N citric acid and is dried over magnesium sulphate. An oily product remains after removal of the solvent.

Yield: 6.4 g oil b) 2-Thienyl-N-aminoacetylaminoacetic acid hydrochloride

A solution of 9 g of the compound from Example (9a) in 50 ml of glacial acetic acid is saturated with gaseous HCl while cooling in ice. The mixture is allowed to reach room temperature while stirring, during which a precipitate forms, and this is filtered off with suction. The solid is taken up in a little methanol and boiled with a little active charcoal. After filtration, the product is precipitated by addition of diethyl ether and is filtered off with suction.

Yield: 2.2 g melting point 197° C. (decomposition)

EXAMPLE 10

2-Thienyl-N-ethoxycarbonylmethylaminoacetamide is obtained in analogy to Example 7 from 15.6 g of 2-thienylaminoacetamide and 16.7 g of ethyl bromoacetate.

Yield: 6.8 g melting point 120°–122° C.

EXAMPLE 11

N-2-Thienylaminoacetyl)glycine a) N-(2-Thienylhydroximinoacetyl)glycine 17.6 g of powdered sodium hydroxide are added in portions to a mixture of 22 g of 2-thienylglyoxylic acid N-hydroxycarbonylmethyl-amide (prepared from aminoacetic acid and ethyl 2-thienylglyoxylate, melting point 168°–170° C.), 15 ml of water, 50 ml of methanol and 9.5 g of hydroxylamine hydrochloride. The temperature is maintained at 40°–50° C. by cooling and the mixture is then stirred at room temperature for 2 h. It is acidified with concentrated hydrochloric acid and then the volatile fractions are stripped off in a rotary evaporator. The residue is boiled with 300 ml of ethanol and filtered with active charcoal, and the filtrate is concentrated in vacuo. The residue is stirred with diethyl ether and filtered off with suction.

Yield: 7.0 g melting point 175°–177° C.

b) N-(2-Thienylaminoacetyl)glycine

A solution of 11.4 g of 2-thienylhydroximinoacetylglycine and 7 ml of ammonia in 100 ml of methanol is hydrogenated with Raney nickel as catalyst at 100° C./50 bar in an autoclave until hydrogen uptake ceases. The catalyst is filtered off with suction, and the filtrate is concentrated in vacuo. The residue is suspended in 100 ml of ethanol and heated, and just sufficient water is added to produce a clear solution. Then active charcoal is added and, after filtration, the solution is cooled in an ice bath. The precipitate is filtered off with suction and dried.

Yield 7.8 g melting point 208° C. (decomposition)

EXAMPLE A

Emulsions containing 3 mg of active compound per 5 ml can be produced using the following formula:

| | |
|---|---|
| Active compound | 0.06 g |
| Neutral oil | q.s. |
| Sodium carboxymethylcellulose | 0.6 g |
| Polyoxyethylene stearate | q.s. |
| Pure glycerol | 0.2 to 2 g |
| Perfumes | q.s. |
| Water (demineralized or distilled) | ad 100 ml |

EXAMPLE B

Tablets can be produced using the following formulation:

| | |
|---|---|
| Active compound | 2 mg |
| Lactose | 60 mg |
| Maize starch | 30 mg |
| Soluble starch | 4 mg |
| Magnesium stearate | 4 mg |
| | 100 mg |

EXAMPLE C

The following composition is suitable for the production of soft gelatin capsules containing 5 mg of active compound per capsule:

| | |
|---|---|
| Active compound | 5 mg |
| Mixture of triglycerides from coconut oil | 150 mg |
| Capsule contents | 155 mg |

EXAMPLE D

The following formulation is suitable for the production of coated tablets:

| | |
|---|---|
| Active compound | 3 mg |
| Maize starch | 100 mg |
| Lactose | 55 mg |
| sec. Calcium phosphate | 30 mg |
| Soluble starch | 3 mg |
| Magnesium stearate | 5 mg |
| Colloidal silica | 4 mg |

EXAMPLE E

Coated tablets containing an active compound according to the invention and another therapeutically active compound:

| Active compound | 6 mg |
|---|---|
| Propranolol | 40 mg |
| Lactose | 90 mg |
| Maize starch | 90 mg |
| sec. Calcium phosphate | 34 mg |
| Soluble starch | 3 mg |
| Magnesium stearate | 3 mg |
| Colloidal silica | 4 mg |
| | 270 mg |

EXAMPLE F

Coated tablets containing an active compound according to the invention and another therapeutically active compound:

| Active compound | 5 mg |
|---|---|
| Pirlindole | 5 mg |
| Lactose | 60 mg |
| Maize starch | 90 mg |
| sec. Calcium phosphate | 30 mg |
| Soluble starch | 3 mg |
| Magnesium stearate | 3 mg |
| Colloidal silica | 4 mg |
| | 200 mg |

EXAMPLE G

Capsules containing an active compound according to the invention and another therapeutically active compound:

| Active compound | 5 mg |
|---|---|
| Nicergoline | 5 mg |
| Maize starch | 185 mg |
| | 195 mg |

EXAMPLE H

Injection solutions containing 1 mg of active compound per ml can be produced using the following formula:

| Active compound | 1.0 mg |
|---|---|
| Polyethylene glycol 400 | 0.3 mg |
| Sodium chloride | 2.7 mg |
| Water for injections to | 1 ml |

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

What is claimed is:

1. Thienylacetic acid compounds of the general formula I

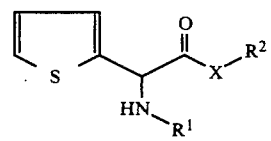

in which

X denotes —O— or —NH—;

$R^1$ and $R^2$ independently denote hydrogen, the group —CH$_2$—CO—$R^3$ or the group —CO—CH$_2$—NH$_2$; and $R^3$ denotes (C$_1$-C$_4$)-alkoxy, hydroxyl or amino, it not being possible for both $R^1$ and $R^2$ to represent hydrogen, as well as the pharmaceutically tolerated salts thereof.

2. Thienylacetic acid compounds according to claim 1, characterized in that

X denotes —O—;

$R^1$ denotes the group —CH$_2$—CO—$R^3$;

$R^2$ denotes hydrogen or (C$_1$-C$_4$)-alkyl and $R^3$ denotes (C$_1$-C$_4$)-alkoxy, hydroxyl or amino.

3. Thienylacetic acid compounds according to claim 1, characterized in that

X denotes —NH—;

$R^1$ denotes the group —CH$_2$—CO—$R^3$;

$R^2$ denotes hydrogen and $R^3$ denotes (C$_1$-C$_4$)-alkoxy or hydroxyl.

4. 2-Thienyl-N-aminocarbonylmethylaminoacetic acid having the structure

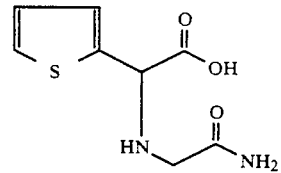

5. 2-Thienyl-N-hydroxycarbonylmethylaminoacetamide hydrochloride having the structure

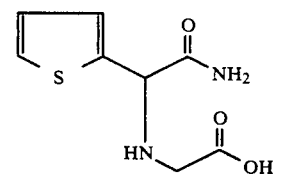

6. Pharmaceutical composition containing as active compound one or more thienylacetic acid derivatives according to claim 1 or a pharmaceutically tolerated salt thereof together with one or more pharmaceutically acceptable additives.

* * * * *